United States Patent [19]
Heine et al.

[11] Patent Number: 6,060,482
[45] Date of Patent: May 9, 2000

[54] TRIAZASPIRODECANONE-METHYLCHROMANS

[75] Inventors: Hans-Georg Heine, Krefeld; Rudolf Schohe-Loop, Wuppertal; Thomas Glaser, Overath; Jean Marie Viktor de Vry, Rösrath; Wolfgang Dompert; Henning Sommermeyer, both of Köln, all of Germany

[73] Assignee: Bayer Aktiengesellschaft, Leverkusen, Germany

[21] Appl. No.: 07/963,165

[22] Filed: Oct. 19, 1992

[30] Foreign Application Priority Data

Oct. 28, 1991 [DE] Germany ............................. 41 35 473

[51] Int. Cl.[7] .......................... A61K 31/44; C07D 471/20
[52] U.S. Cl. ............................................. 514/278; 546/20
[58] Field of Search ................................. 546/20; 514/278

[56] References Cited

U.S. PATENT DOCUMENTS

| 3,759,927 | 9/1973 | Huebner | 546/20 |
| 3,826,835 | 7/1974 | Huebner | 514/318 |
| 3,845,060 | 10/1974 | Huebner | 546/20 |
| 4,689,330 | 8/1987 | Janssens et al. | 514/321 |
| 4,749,702 | 6/1988 | Janssens et al. | 514/253 |
| 4,826,848 | 5/1989 | Janssens et al. | 514/258 |
| 4,957,928 | 9/1990 | Fröstl et al. | 514/318 |
| 5,112,855 | 5/1992 | Fröstl et al. | 514/456 |

FOREIGN PATENT DOCUMENTS

| 0352613 | 1/1990 | European Pat. Off. . |
| 0360077 | 3/1990 | European Pat. Off. . |
| 4039631 | 6/1992 | Germany . |

OTHER PUBLICATIONS

European Journal of Medicinal Chemistry Chimica therapeutica, vol. 9, No. 2, Mar. 1974, Chatenay–Malabry FR, pp. 128–132; J. Maillard et al. Composes cycloalcanespiro–heterocycliques XI . . . pp. 131–132.

Farmaco, Ed. Sci. 42(11), 805–13 (1987).
Eur. J. Med. Chem 22(6), 539–44 (1987).
Eur. J. Med. Chem.–Chim. Ther. 20(2), 117–20 (1985).
Brain Research, vol. 578, No. 1–2, Mar. 24, 1992, pp. 1–7.
STN International, Karlsruhe, File 'Phar', Pharmaprojects. AN=8688 Phar. "Pelanserin". (1990).
STN International, Karlsruhe, File 'CA', Chemical Abstracts. AN=CA115 (17) :180699j. M. Ohno (1993).
Nouv. J. Chim. 6(3), 149–154 (1982).
CAS 1021–25–6 (1991).
W.U. Dompert et al., Naunyn–Schmeideberg's Arch. Pharmacol. (1985), 328, 467–470.
Imafuku J. (1987), Brain Research 402, 331–338.
Still et al, J. Org. Chem. 43, 2923, 1978.
Aldrichimica Acta 18, 25, 1985.
Barchas et al "Serotonin and Behavior" Aca. Press. p. 235 (1973).
Glennon R A "Central Serotonin Receptors as Target for drug research" J. Med Chem. 30(1) 1–12 (1987).
Matthews et al "Fundamentals of Receptors, Enzymes and Transport Kinetics" CRC Press, pp. 25–29 (1993).
Gennaro A. "Remington's Pharmaceutical Science" Mark Publishing Co. pp. 702–705 (1990).
O'Brien R.A "Receptor Binding in Drug Research" Marcel Dekker, Inc. pp. 94–96 (1987).
Traber et al "5–HTIA receptor–related auxiolytics" TIPS (8) pp. 432–437 (1987).
Hackh's "Chemical Dictionary" p. 16 (1983).

*Primary Examiner*—Ceila Chang
*Attorney, Agent, or Firm*—Norris, McLaughlin & Marcus, P.A.

[57] ABSTRACT

Triazaspirodecanone-methylchromans are prepared by reacting methylchromans, which are substituted on the methyl group by appropriate leaving groups, with triazaspirodecanones. The substances can be employed for the production of medicaments, in particular for medicaments for the control of disorders of the central nervous system.

10 Claims, No Drawings

TRIAZASPIRODECANONE-METHYLCHROMANS

The invention relates to new 1,3,8-triazaspiro[4.5]decan-4-one-2-methylchromans, to a process for their preparation and to their use in medicaments, in particular as agents for the control of diseases of the central nervous system.

DE 2,165,276 discloses 1,3,8-triazaspiro[4.5]decan-4-one-substituted 2-methyl-benzofurans. In addition U.S. Pat. No. 3,826,835 describes 8-benzofurylmethyl-1,3,8-triazaspiro-[4.5]decanes as neuroleptics.

The invention relates to 1,3,8-triazaspiro[4.5]decan-4-one-2-methylchromans of the general formula (I)

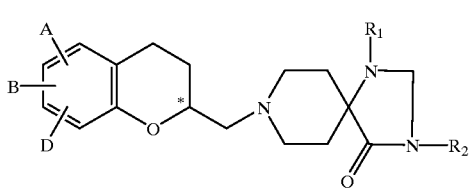

in which

A, B and D are identical or different and represent hydrogen, halogen, cyano, azido, nitro, difluoromethyl, trifluoromethyl, difluoromethoxy, trifluoromethoxy, hydroxyl or carboxyl, or represent straight-chain or branched alkyl, alkenyl, acyl or alkoxycarbonyl each having up to 8 carbon atoms, or represent a group of the formula —NR$^3$R$^4$, —NR$^5$—L—R$^6$ or —OR$^7$, in which R$^3$, R$^4$ and R$^5$ are identical or different and denote hydrogen, straight-chain or branched alkyl having up to 8 carbon atoms, phenyl or benzyl, L denotes the —CO— or —SO$_2$— group, R$^6$ denotes straight-chain or branched alkyl having up to 8 carbon atoms or benzyl, or denotes aryl having 6 to 10 carbon atoms, which is optionally substituted by halogen, hydroxyl, nitro, cyano, trifluoromethyl, trifluoromethoxy or by straight-chain or branched alkyl or alkoxy each having up to 6 carbon atoms, R$^7$ denotes straight-chain or branched alkyl or alkenyl each having up to 8 carbon atoms, each of which is optionally substituted by cycloalkyl having 3 to 6 carbon atoms or phenyl or A has one of the abovementioned meanings and B and D together form a 5- to 7-membered saturated, partially unsaturated or aromatic carbocyclic ring or heterocyclic ring having up to 2 heteroatoms from the series comprising S, N and O, where these rings can optionally have up to 2 carbonyl functions in the ring and are optionally monosubstituted or disubstituted by identical or different substituents from the series comprising straight-chain or branched alkyl or alkoxy each having up to 6 carbon atoms, hydroxyl, cycloalkyl having 3 to 6 carbon atoms, phenyl, halogen, cyano, nitro or in spiro fashion by a radical of the formula,

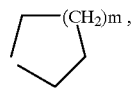

in which m denotes a number 1 or 2, and

R$^1$ and R$^2$ are identical or different and represent hydrogen or straight-chain or branched alkyl, or represent phenyl or benzyl, each of which is optionally monosubstituted to trisubstituted by identical or different substituents from the series comprising halogen, hydroxyl, cyano, difluoromethyl, difluoromethoxy, trifluoromethyl and trifluoromethoxy or by straight-chain or branched alkyl or alkoxy each having up to 8 carbon atoms, if appropriate in an isomeric form, and their salts.

In the context of the present invention, physiologically acceptable salts are preferred. Physiologically acceptable salts of the substituted 1,3,8-triazaspiro[4.5]-decan-4-one-2-methylchromans can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts in the context of the present invention are additionally salts of the univalent metals, such as alkali metals, and the ammonium salts. Sodium salts, potassium salts and ammonium salts are preferred.

In the context of the present invention, the compounds according to the invention can exist in various stereoisomeric forms. The compounds according to the invention exist in stereoisomeric forms which behave either as image and mirror image (enantiomers), or which do not behave as image and mirror image (diastereomers). The invention relates both to the antipodes and to the racemic forms as well as the diastereomer mixtures. Like the diastereomers, the racemic forms can be separated into the stereoisomerically uniform constituents in a known manner [cf. E. L. Eliel, Stereochemistry of Carbon Compounds, McGraw Hill, 1962].

Preferred compounds of the general formula (I) are those in which

A, B and D are identical or different and represent hydrogen, fluorine, chlorine, bromine, cyano, trifluoromethyl, difluoromethoxy, trifluoromethoxy or hydroxyl, or represent straight-chain or branched alkyl, alkenyl, acyl or alkoxycarbonyl each having up to 6 carbon atoms, or represent a group of the formula —NR$^3$R$^4$, —NR$^5$—L—R$^6$ or —OR$^7$, in which R$^3$, R$^4$ and R$^5$ are identical or different and denote hydrogen or straight-chain or branched alkyl having up to 6 carbon atoms, L denotes the —CO— or —SO$_2$— group, R$^6$ denotes straight-chain or branched alkyl having up to 6 carbon atoms or benzyl, or denotes phenyl which is optionally substituted by fluorine, chlorine, bromine, trifluoromethyl, trifluoromethoxy, hydroxyl or by straight-chain or branched alkyl or alkoxy each having up to 4 carbon atoms, $R^7$ denotes straight-chain or branched alkyl or alkenyl having up to 6 carbon atoms, each of which is optionally substituted by cyclopropyl, cyclopentyl, cyclohexyl or phenyl, or A has one of the abovementioned meanings and B and D together form a radical of the formula

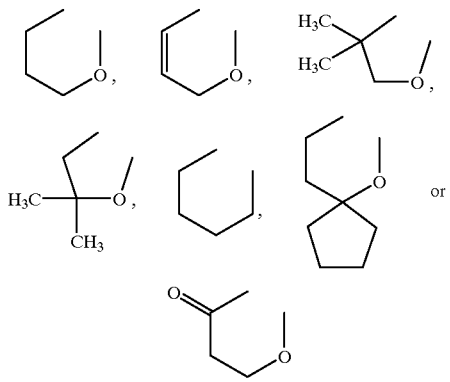

$R^1$ and $R^2$ are identical or different and represent hydrogen or straight-chain or branched alkyl having up to 6 carbon atoms, or represent phenyl or benzyl, each of which is optionally monosubstituted or disubstituted by identical or different substituents from the series comprising fluorine, chlorine, bromine, hydroxyl, cyano, trifluoromethyl and trifluoromethoxy or by straight-chain or branched alkyl or alkoxy each having up to 6 carbon atoms, if appropriate in an isomeric form, and their salts.

Particularly preferred compounds of the general formula (I) are those in which

A, B and D are identical or different and represent hydrogen, fluorine, chlorine, bromine, cyano, trifluoromethyl, trifluoromethoxy or hydroxyl, represent straight-chain or branched alkyl or alkenyl each having up to 4 carbon atoms, represent a group of the formula $-NR^2R^3$ or $-OR^6$, in which $R^2$ and $R^3$ are identical or different and denote hydrogen or straight-chain or branched alkyl having up to 4 carbon atoms, $R^6$ denotes straight-chain or branched alkyl or alkenyl having up to 4 carbon atoms, each of which is optionally substituted by cyclopropyl or phenyl, or A has one of the abovementioned meanings and B and D together denote a radical of the formula

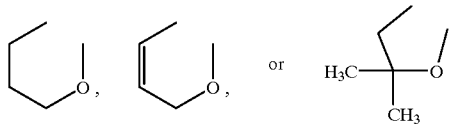

$R^1$ and $R^2$ are identical or different and represent hydrogen or straight-chain or branched alkyl having up to 4 carbon atoms, or represent phenyl or benzyl, each of which is optionally substituted by fluorine, chlorine, bromine, hydroxyl, trifluoromethyl or trifluoromethoxy or by straight-chain or branched alkyl or alkoxy each having up to 4 carbon atoms, if appropriate in an isomeric form, and their salts.

Very particularly preferred compounds of the general formula (I) are those in which A, B and D represent hydrogen or methoxy, $R^1$ represents phenyl and $R^2$ represents hydrogen.

In addition, a process for the preparation of the compounds of the general formula (I) according to the invention has been found, characterised in that compounds of the general formula (II)

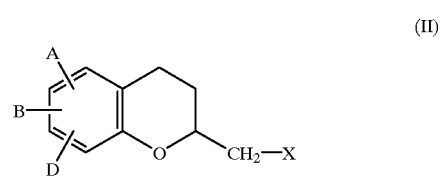

(II)

in which

A, B and D have the abovementioned meaning and

X represents hydroxyl or a typical leaving group, such as tosyloxy, mesyloxy, chlorine or bromine, are reacted in inert solvents, in the presence of a base and if appropriate of a catalyst, with compounds of the general formula (III)

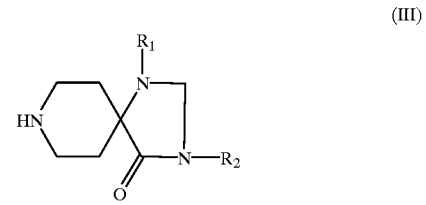

(III)

in which $R^1$ and $R^2$ have the abovementioned meaning, and if appropriate the substituents A, B and D are varied according to a customary method.

The process according to the invention can be illustrated by way of example by the following reaction scheme:

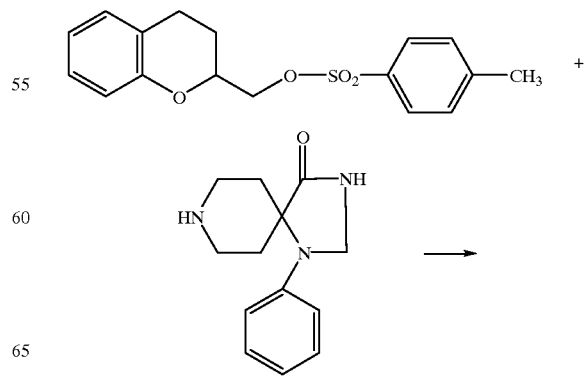

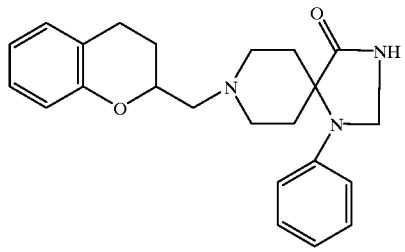

Suitable solvents are the customary solvents which do not change under the reaction conditions. These preferably include alcohols such as methanol, ethanol, propanol or isopropanol, or ethers such as diethyl ether, dioxane, tetrahydrofuran, glycol dimethyl ether or butyl methyl ether, or ketones such as acetone or butanone, or amides such as dimethylformamide or hexamethylphosphoric triamide, or dimethylsulphoxide, acetonitrile, ethyl acetate, or halogenohydrocarbons such as methylene chloride, chloroform or carbon tetrachloride, or pyridine, picoline or N-methylpiperidine. Mixtures of the solvents mentioned can also be used. Dimethylformamide is preferred.

Suitable bases are the customary inorganic or organic bases. These preferably include alkali metal hydroxides such as, for example, sodium hydroxide or potassium hydroxide, or alkali metal carbonates such as sodium carbonate or potassium carbonate, or alkali metal alkoxides such as, for example, sodium methoxide or potassium methoxide, or sodium ethoxide or potassium ethoxide, or organic amines such as triethylamine, picoline or N-methylpiperidine, or amides such as sodium amide or lithium diisopropylamide, or organometallic compounds such as butyllithium or phenyllithium. Sodium carbonate and potassium carbonate and triethylamine are preferred.

The base is employed in an amount from 0.6 mol to 5 mol, preferably from 0.7 mol to 2 mol relative to 1 mol of the compound of the general formula (II).

The reaction is in general carried out in a temperature range from 0° C. to 150° C., preferably from +20° C. to +110° C.

The reaction can be carried out at normal, elevated or reduced pressure (for example 0.5 to 5 bar). In general, it is carried out at normal pressure.

Suitable catalysts are in general alkali metal halides such as, for example, sodium iodide or potassium iodide. Sodium iodide is preferred.

The catalyst is in general employed in an amount from 0.05–1.0 mol, preferably from 0.1 to 0.5 mol, relative to 1 mol of the compounds of the general formula (II).

The compounds of the general formula (II) are known or can be prepared by a customary method [cf. U.S. Pat. No. 4,957,928; Farmaco, Ed. Sci. 42 (11), 805–13; Eur. J. Med. Chem. 22 (6), 539–44; EP 252,005; EP 199,400; Eur. J. Med. Chem.-Chim. Ther. 20(2), 117–20; Nouv. J. Chim. 6(3), 149–154].

The compounds of the general formula (III) are also known [cf. U.S. Pat. No. 3,826,835]; [CAS, 1021-25-6].

The compounds according to the invention can be used as active substances in medicaments. The substances according to the invention have a particularly high affinity for cerebral 5-hydroxy-tryptamine receptors of the 5-$HT_1$ type. They also have high affinity for dopamine receptors of the $D_2$ type.

The substances according to the invention surprisingly exhibit an advantageous action on the central nervous system and can be used for the therapeutic treatment of humans and animals.

The compounds described in the present invention thus represent active substances for the control of diseases which are characterised by disorders of the serotoninergic and dopaminergic system, in particular with the involvement of receptors which have high affinity for 5-hydroxytryptamine (5-$HT_1$ type) and/or for dopamine ($D_2$ type). They are therefore suitable for the treatment of disorders of the central nervous system such as anxiety, tension and depression states, central nervous system-related sexual dysfunctions and sleep disorders, and for controlling morbid disorders of the intake of food, stimulants and tobacco and addictive drugs. They are additionally suitable for the elimination of cognitive deficits, for the improvement of learning and memory power and for the treatment of Alzheimer's disease. They are also suitable for the control of psychoses (for example schizophrenia, mania). Compared to known neuroleptics, they have a lower side effect potential.

In addition, these active substances are also suitable for the modulation of the cardiovascular system. They also intervene in the regulation of the cerebral circulation and thus represent effective agents for the control of migraine.

They are also suitable for the prophylaxis and control of the sequelae of occurrences of cerebral infarct (apoplexia cerebri) such as stroke and cerebral ischaemia. In addition the compounds according to the invention can be used for the treatment of acute cranio-cerebral trauma and also for the control of pain states.

Affinity for the 5-$HT_1$ receptor

In Table 1, the high affinity of the compounds according to the invention for 5-hydroxytryptamine receptors of the subtype 1 is represented by way of example. The values given are data which have been determined from receptor binding studies using calf hippocampus membrane preparations. The radioactively labelled ligand used for this was $^3$H-serotonin.

TABLE A

| Compound of example | $K_i$(nmol/l) |
|---|---|
| 1 | 2 |
| 2 | 1.5 |
| 4 | 1 |

Affinity for the 5-$HT_{1A}$ receptor

[W. U. Dompert et al., Naunyn-Schmiedeberg's Arch. Pharmacol. (1985), 328, 467–470].

In this test, the binding of $^3$H-ipsapirone to 5-$HT_{1A}$ receptors in calf hippocampus membranes is measured. It was found that the compounds according to the invention compete with the radioligand for binding and inhibit this.

TABLE B

| Compound of example | $K_i$(nmol/l) |
|---|---|
| 5 | 1 |
| 6 | 1 |

Dopamine $D_2$ receptor test

This test is carried out according to the following reference: Imafuku J. (1987), Brain Research 402; 331–338.

In this test, the binding of the selective $D_2$-receptor antagonist $^3$H-sulpiride on membranes from the striatum of the rat is measured. Compounds which bind to dopamine $D_2$-receptors inhibit the binding of $^3$H-sulpiride in a concentration-dependent manner. $IC_{50}$ values are determined from the displacement curves and the inhibition constants $K_i$ are calculated from these.

TABLE C

| Compound of example | $K_i$(nmol/l) |
|---|---|
| 1 | 0.2 |
| 2 | 0.3 |
| 3 | 0.6 |

The present invention also includes pharmaceutical preparations which, in addition to inert, non-toxic, pharmaceutically suitable auxiliaries and excipients, contain one or more compounds of the general formula (I), or which consist of one or more active substances of the formula (I), and processes for the production of these preparations.

The active substances of the formula (I) should be present in these preparations in a concentration from 0.1 to 99.5% by weight, preferably from 0.5 to 95% by weight of the total mixture.

In addition to the active substances of the formula (I), the pharmaceutical preparations can also contain other pharmaceutical active substances.

The abovementioned pharmaceutical preparations can be prepared in a customary manner by known methods, for example using the auxiliary(ies) or excipient(s).

In general, it has proved advantageous to administer the active substance(s) of the formula (I) in total amounts from about 0.01 to about 100 mg/kg, preferably in total amounts of about 0.1 mg/kg to 5 mg/kg of bodyweight every 24 hours, if appropriate in the form of several individual doses, to achieve the desired result.

However, it may be advantageous to depart from the amounts mentioned, in particular depending on the nature and the bodyweight of the subject treated, on individual behaviour towards the medicament, the nature and severity of the disease, the type of preparation and administration, and the time or interval at which administration takes place.

The $R_f$ values shown in each case were determined—if not stated otherwise—by thin layer chromatography on silica gel (aluminium foil, silica gel 60 F 254, E. Merck). The visualisation of the substance spots was carried out by examining under UV light and/or by spraying with 1% strength potassium permanganate solution.

Flash chromatography was carried out on silica gel 60, 0.040–0.064 mm, E. Merck (see Still et al., J. Org. Chem. 43, 2923, 1978; for simpler separation problems see Aldrichimica Acta 18, 25, 1985). Elution with solvent gradient means: beginning with the pure, non-polar solvent mixture component the polar eluent component is admixed to an increasing extent until the desired product is eluted (TLC checking).

In the case of all products, the solvent was distilled off at the end at about 0.1 mm Hg. Salts were kept at this pressure overnight over potassium hydroxide and/or phosphorus pentoxide.

Starting Compounds

Example I
2-Hydroxymethyl-8-methoxy-chroman

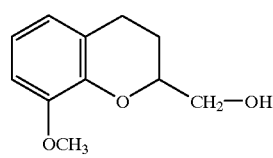

59.0 g (0.25 mol) of ethyl 8-methoxy-chroman-2-carboxylate are added dropwise in 525 mol of anhydrous tetrahydrofuran in the course of 1 h with stirring at 20° C. to the suspension from 9.5 g (0.25 mol) of lithium aluminium hydride in 525 ml of anhydrous diethyl ether. The mixture is stirred overnight and then treated drop-wise successively with cooling with 9.5 ml of water, 9.5 ml of 15% strength sodium hydroxide solution and 28.4 ml of water. The organic phase is decanted and evaporated. The residue is recrystallised twice from dichloromethane/petroleum ether.

Yield: 38.0 g (87%)
M.p.: 57–58° C.

Example II
(2R)-2-Hydroxymethyl-chroman

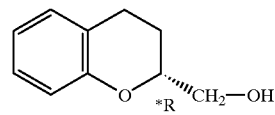

164 ml of a 1 M borane solution in tetrahydrofuran are added dropwise at an internal temperature of 0° C. to the solution from 22.1 g (0.124 mol) of (2R)-chroman-2-carboxylic acid (ee=98.3%) in 210 ml of anhydrous tetrahydrofuran under argon in the course of 30 minutes. The cooling is removed and the batch is subsequently stirred for 4 h. The internal temperature rises during the course of this to 34° C. 46 ml of a 1/1 mixture of tetrahydrofuran and water are then added dropwise with ice-cooling. After addition of 40.7 g of anhydrous potassium carbonate and vigorous stirring, the tetrahydrofuran solution is decanted and concentrated in a water jet vacuum. Short path distillation yields 18.8 g of colourless 2R-hydroxymethylchroman of b.p. 77–78° C./0.15 mbar.
ee>99%.

Example III
(2S)-2-Hydroxymethyl-chroman

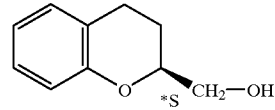

The title compound is prepared from (2S)-chroman-2-carboxylic acid in analogy to the procedure of Example II.
ee>99%
B.p.: 79–81° C./0.15 mbar.

Example IV
(2R)-2-Tosyloxymethyl-chroman

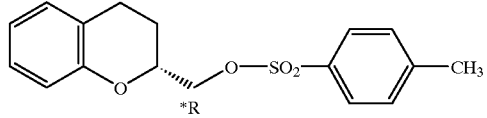

15.63 g of 4-toluenesulphonyl chloride are added in portions with stirring and ice-cooling to 12.8 g (0.78 mol) of (2R)-2-hydroxymethylchroman (Example II) in 50 ml of anhydrous pyridine. After allowing to stand overnight, the mixture is introduced into ice-water and extracted with diethyl ether. The ether phase is washed twice with 5% strength ice-cold hydrochloric acid and then with saturated sodium chloride solution, dried over anhydrous sodium sulphate and evaporated in a water jet vacuum. 22.4 g of homogeneous 4-toluenesulphonate of 2R-2-hydroxymethylchroman are obtained.

$R_f$=0.6 (toluene/ethyl acetate 3:1) oil, $[\alpha]_D$=51.1° (c=1, CHCl$_3$) M.p. °C.=61.5–64.5 (from dichloromethane/petroleum ether).

Example V
(2S)-2-Tosyloxymethyl-chroman

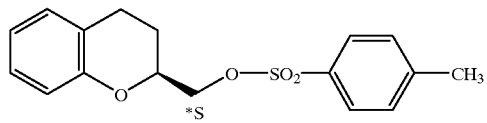

The title compound is prepared from Example III in analogy to the procedure of Example IV.

$R_f$=0.6 (toluene/ethyl acetate 3:1) oil

Example VI
8-Methoxy-2-tosyloxymethyl-chroman

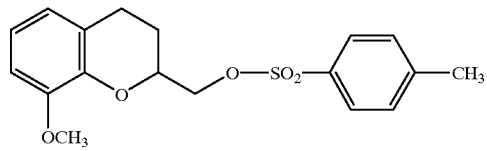

M.p.: 115–117° C. (from dichloromethane).

PREPARATION EXAMPLES

Example 1

8-(Chroman-2-yl-methyl)-1-phenyl-1,3,8-triazaspiro[4.5]-decan-4-one

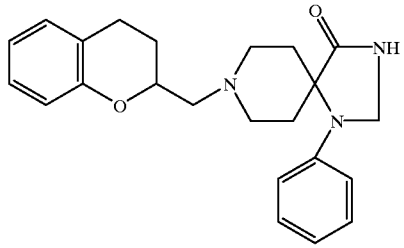

The mixture from 31.8 g (0.1 mol) of 2-tosyloxymethyl-chroman, 7.1 g (0.07 mol) of anhydrous sodium carbonate and 23.1 g (0.1 mol) of 1-phenyl-1,3,8-triazaspiro[4.5]-decan-4-one in 240 mol of anhydrous dimethylformamide (DMF) is stirred at 110° C. for 6 h and then poured onto ice (500 g). After extracting with ethyl acetate (5×100 ml), washing the organic extracts with water, drying over anhydrous sodium sulphate and evaporating the organic phase in a water jet vacuum, 65.7 g of solvent-containing crystalline crude product are obtained which, recrystallised twice from ethyl acetate, yields 20.6 g of the title compound of m.p. 192–193.5° C.

Yield: 55% of theory.

The Examples shown in Table 1 are prepared in analogy to the procedure of Example I:

TABLE 1

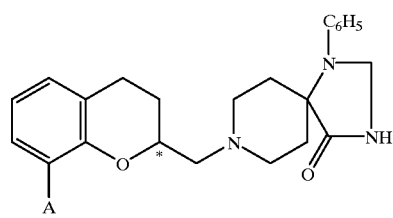

| Ex. No. | A | * | M.p. ° C. | ee (%) | α (D)° |
|---|---|---|---|---|---|
| 2 | —OCH$_3$ | R, S | 169–172 | — | — |
| 3 | H | S | 170.5–172 | >98 | +56.0 (c = 1, THF) |
| 4 | H | R | 171–173 | >98 | −52.5 (c = 1, THF) |

Example 5

8-(Chroman-2-yl-methyl)-1-phenyl-1,3,8-triazaspiro[4.5]-decan-4-one HCl salt

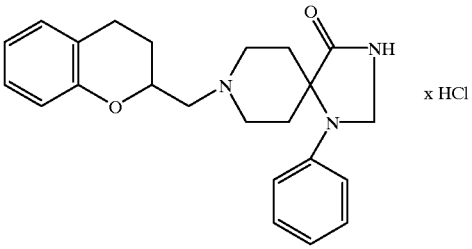

3.34 g (0.01 mol) of 8-(chroman-2-yl-methyl)-1-phenyl-1,3,8-triazaspiro[4.5]decan-4-one are dissolved in 100 ml of diethyl ether with the addition of 20 ml of dichloro-methane and treated with stirring with 6.9 ml of 1.45 N etherial hydrochloric acid with ice-cooling. After 2 h, the precipitate is filtered off with suction, washed with diethyl ether and dried in an oil pump vacuum at 60° C. 3.4 g of the title compound of m.p. 238–240° C. (capillary) are obtained.

The compounds shown in Table 2 are prepared in analogy to the procedure of Example 5:

TABLE 2

| Ex. No. | A | M.p. ° C. | |
|---|---|---|---|
| 6 | —OCH$_3$ | 250–252 | |
| 7 | H | 250–254 | Configuration at C-2: R |

We claim:

1. Triazaspirodecanone-methylchromans of the general formula (I)

[structure of chroman fused system with substituents A, B, D and spiro piperidine-imidazolidinone with R₁, R₂]

in which
- A, B and D are identical or different and represent hydrogen, halogen, cyano, azido, nitro, difluoromethyl, trifluoromethyl, difluoromethoxy, trifluoromethoxy, hydroxyl or carboxyl, or
- represent straight-chain or branched alkyl, alkenyl, acyl or alkoxycarbonyl each having up to 8 carbon atoms, or
- represent a group of the formula $-NR^3R^4$, $-NR^5-L-R^6$ or $-OR^7$, in which
- $R^3$, $R^4$ and $R^5$ are identical or different and denote hydrogen, straight-chain or branched alkyl having up to 8 carbon atoms, phenyl or benzyl,
- L denotes the $-CO-$ or $-SO_2-$ group,
- $R^6$ denotes straight-chain or branched alkyl having up to 8 carbon atoms or benzyl, or
- denotes aryl having 6 to 10 carbon atoms, which is optionally substituted by halogen, hydroxyl, nitro, cyano, trifluoromethyl, trifluoromethoxy or by straight-chain or branched alkyl or alkoxy each having up to 6 carbon atoms,
- $R^7$ denotes straight-chain or branched alkyl or alkenyl each having up to 8 carbon atoms, each of which is optionally substituted by cycloalkyl having 3 to 6 carbon atoms or phenyl or
- A has one of the abovementioned meanings and
- B and D together form a 5- to 7-membered saturated, partially unsaturated or aromatic carbocyclic ring or heterocyclic ring having up to 2 heteroatoms from the series comprising S, N and O, where these rings can optionally have up to 2 carbonyl functions in the ring and are optionally monosubstituted or disubstituted by identical or different substituents from the series comprising straight-chain or branched alkyl or alkoxy each having up to 6 carbon atoms, hydroxyl, cycloalkyl having 3 to 6 carbon atoms, phenyl, halogen, cyano, nitro or in spiro fashion by a radical of the formula

[cyclic structure with $-(CH_2)_m$]

in which
- m denotes a number 1 or 2, and
- $R^1$ and $R^2$ are identical or different and represent hydrogen or straight-chain or branched alkyl, or
- represent phenyl or benzyl, each of which is optionally monosubstituted to trisubstituted by identical or different substituents from the selected from the group consisting of halogen, hydroxyl, cyano, difluoromethyl, difluoromethoxy, trifluoromethyl and trifluoromethoxy or by straight-chain or branched alkyl or alkoxy each having up to 8 carbon atoms, if appropriate in an isomeric form, and their salts.

2. Triazaspirodecanone-methylchromans according claim 1 where
- A, B and D are identical or different and represent hydrogen, fluorine, chlorine, bromine, cyano, trifluoromethyl, difluoromethoxy, trifluoromethoxy or hydroxyl, or
- represent straight-chain or branched alkyl, alkenyl, acyl or alkoxycarbonyl each having up to 6 carbon atoms, or
- represent a group of the formula $-NR^3R^4$, $-NR^5-L-R^6$ or $-OR^7$, in which
- $R^3$, $R^4$ and $R^5$ are identical or different and denote hydrogen or straight-chain or branched alkyl having up to 6 carbon atoms,
- L denotes the $-CO-$ or $-SO_2-$ group,
- $R^6$ denotes straight-chain or branched alkyl having up to 6 carbon atoms or benzyl, or
- denotes phenyl which is optionally substituted by fluorine, chlorine, bromine, trifluoromethyl, trifluoromethoxy, hydroxyl or by straight-chain or branched alkyl or alkoxy each having up to 4 carbon atoms,
- $R^7$ denotes straight-chain or branched alkyl or alkenyl having up to 6 carbon atoms, each of which is optionally substituted by cyclopropyl, cyclopentyl, cyclohexyl or phenyl, or
- A has one of the abovementioned meanings and
- B and D together form a radical of the formula

[six structures depicted: tetrahydropyran-like, dihydropyran, gem-dimethyl variants, cyclopentane-spiro, and lactone structures]

- $R^1$ and $R^2$ are identical or different and represent hydrogen or straight-chain or branched alkyl having up to 6 carbon atoms, or
- represent phenyl or benzyl, each of which is optionally monosubstituted or disubstituted by identical or different substituents from the selected from the group consisting of fluorine, chlorine, bromine, hydroxyl, cyano, trifluoromethyl and trifluoromethoxy or by straight-chain or branched alkyl or alkoxy each having up to 6 carbon atoms, if appropriate in an isomeric form, and their salts.

3. Triazaspirodecanone-methylchromans according claim 1 in which
- A, B and D are identical or different and represent hydrogen, fluorine, chlorine, bromine, cyano, trifluoromethyl, trifluoromethoxy or hydroxyl,
- represent straight-chain or branched alkyl or alkenyl each having up to 4 carbon atoms, represent a group of the formula —NR²R³ or —OR⁶, in which R² and R³ are identical or different and denote hydrogen or straight-chain or branched alkyl having up to 4 carbon atoms, R⁶ denotes straight-chain or branched alkyl or alkenyl having up to 4 carbon atoms, each of which is optionally substituted by cyclopropyl or phenyl, or A has one of the abovementioned meanings and B and D together denote a radical of the formula

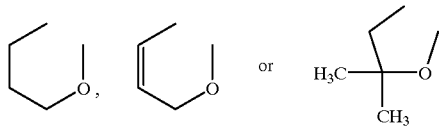

R¹ and R² are identical or different and represent hydrogen or straight-chain or branched alkyl having up to 4 carbon atoms, or represent phenyl or benzyl, each of which is optionally substituted by fluorine, chlorine, bromine, hydroxyl, trifluoromethyl or trifluoromethoxy or by straight-chain or branched alkyl or alkoxy each having up to 4 carbon atoms, if appropriate in an isomeric form, and their salts.

4. A compound according to claim 1 wherein such compound is 8-(chroman-2-yl-methyl)-1-phenyl-1,3,8-triazaspiro[4,5]-decan-4-one of the formula

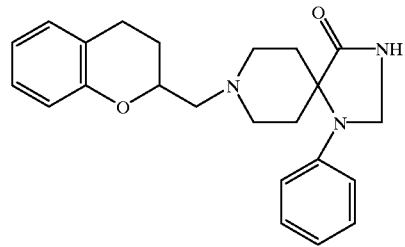

or a salt thereof.

5. A compound according to claim 1 wherein such compound is R-(−)-8-(chroman-2-yl-methyl)-1-phenyl-1,3,8-triazaspiro[4,5]-decan-4-one of the formula

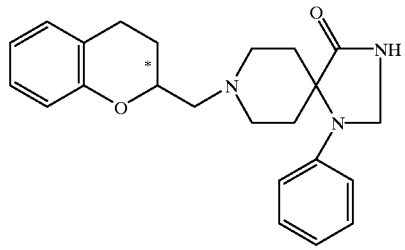

* (−)enantiomer or a salt thereof.

6. A composition for the treatment of diseases of the serotoninergic system related to 5 HT₁ receptors comprising an amount effective therefor of a compound or a salt thereof according to claim 1 and a pharmacologically acceptable diluent.

7. A composition for the treatment of psychoses comprising an amount effective therefor of a compound or salt thereof according to claim 1 and a pharmacologically acceptable diluent.

8. The method of treating diseases which are characterized by disturbances of the serotoninergic system related to 5 HT₁ receptors in a patient in need thereof which comprises administering to such a patient an amount effective therefor of a compound or salt thereof according to claim 1.

9. The method of treating psychoses in a patient in need thereof which comprises administering to such a patient an amount effective therefor of a compound or salt thereof according to claim 1.

10. A method for treating anxiety, tension, or depression in a patient in need thereof by binding with the 5-HT₁ receptor which comprises administering to such patient an amount effective therefor of a compound or salt according to claim 1.

* * * * *

UNITED STATES PATENT AND TRADEMARK OFFICE
CERTIFICATE OF CORRECTION

PATENT NO. : 6,060,482
DATED : May 9, 2000
INVENTOR(S) : Heine et al.

It is certified that error appears in the above-identified patent and that said Letters Patent is hereby corrected as shown below:

Title page,
Item [56], OTHER PUBLICATIONS, insert after "Hackh's "Chemical Dictionary", p.6, (1983)" the following references-March "Organic Chemistry", McGraw Hill Co., p. 607 (1977); Alder "Probability and Statistics", Freeman Co., p. 1-2 (1972); Considine, et al., "Van Nostrand's Scientific Encyclopedia", Van Nostrand Reinhold, p. 2579, (1991) --.

Column 11,
Lines 39-57, cancel "B and D together form a 5– to 7-membered saturated, partially unsaturated or aromatic carbocyclic ring or heterocyclic ring having up to 2 heteroatoms from the series comprising S, N and O, where these rings can optionally have up to 2 carbonyl functions in the ring and are optionally monosubstitued or disubstitute by identical or difference substituents from the series comprising straight-chain or branched alkyl or alkoxy each having up to 6 carbon atoms, hydroxyl, cycloalkyl having 3 to 6 carbon atoms, phenyl, halogen, cyano, nitro or in spiro fashion by a radical of the formula

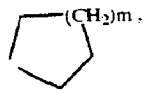

in which m denotes a number 1 or 2, and"

Line 62, delete first occurrence of "from the"

Column 12,
Line 1, add -- to -- after "according"
Lines 29-49, cancel "B and D together form a radical of the formula

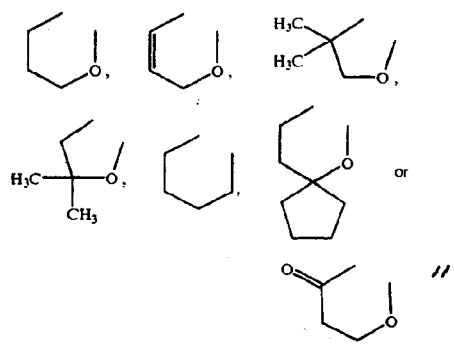

UNITED STATES PATENT AND TRADEMARK OFFICE
CERTIFICATE OF CORRECTION

PATENT NO.    : 6,060,482
DATED         : May 9, 2000
INVENTOR(S)   : Heine et al.

It is certified that error appears in the above-identified patent and that said Letters Patent is hereby corrected as shown below:

Column 12 cont'd,
Line 55, delete first occurrence of "from the"

Column 13,
Lines 11-18, cancel "B and D together denote a radical of the formula

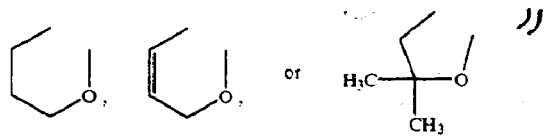

Signed and Sealed this

Twentieth Day of May, 2003

JAMES E. ROGAN
*Director of the United States Patent and Trademark Office*